US009867692B2

(12) United States Patent
Wood et al.

(10) Patent No.: US 9,867,692 B2
(45) Date of Patent: Jan. 16, 2018

(54) CELL SUSPENSION PREPARATION TECHNIQUE AND DEVICE

(71) Applicant: Avita Medical Limited, Melbourn, Royston Herts (GB)

(72) Inventors: Fiona M. Wood, City Beach (AU); Marie L. Stoner, Maida Vale (AU)

(73) Assignee: Avita Medical Ltd., Melbourn (GB)

( * ) Notice: Subject to any disclaimer, the term of this patent is extended or adjusted under 35 U.S.C. 154(b) by 0 days.

(21) Appl. No.: 14/645,933

(22) Filed: Mar. 12, 2015

(65) Prior Publication Data

US 2015/0182739 A1 Jul. 2, 2015

Related U.S. Application Data

(60) Continuation of application No. 13/223,577, filed on Sep. 1, 2011, now Pat. No. 9,078,741, which is a
(Continued)

(30) Foreign Application Priority Data

Feb. 7, 2001 (AU) ........................ PR2989

(51) Int. Cl.
*A61M 37/00* (2006.01)
*A61F 2/10* (2006.01)
(Continued)

(52) U.S. Cl.
CPC .............. *A61F 2/105* (2013.01); *A61K 35/36* (2013.01); *A61M 37/00* (2013.01); *C12M 45/02* (2013.01);
(Continued)

(58) Field of Classification Search
CPC ...... A61F 2/10; A61K 35/36; A61M 2202/09; A61M 2205/7545; A61M 37/00;
(Continued)

(56) References Cited

U.S. PATENT DOCUMENTS 1,356,794 A 10/1920 Smith
3,608,553 A 9/1971 Balamuth
(Continued)

FOREIGN PATENT DOCUMENTS

AU P02752 10/1996
AU 3990197 4/1998
(Continued)

OTHER PUBLICATIONS

Anonymous, "Recell patient leaflet," Absolute Makeover, Apr. 21, 2011, https://www.absolutemakeover.com.au/cosmetic-face-prodedures-perth/recell-spray-on-skin/.
(Continued)

*Primary Examiner* — Jill Warden
*Assistant Examiner* — Jacqueline Brazin
(74) *Attorney, Agent, or Firm* — Greenberg Traurig, LLP; Fang Xie (57) ABSTRACT

The present invention provides for methods and devices suitable for producing a transplantable cellular suspension of living tissue suitable for grafting to a patient. In applying the method and/or in using the device, donor tissue is harvested, subjected to a cell dissociation treatment, cells suitable for grafting back to a patient are collected and dispersed in a solution that is suitable for immediate dispersion over the recipient graft site.

19 Claims, 4 Drawing Sheets

Related U.S. Application Data division of application No. 13/036,569, filed on Feb. 28, 2011, now Pat. No. 9,029,140, which is a continuation of application No. 10/068,299, filed on Feb. 6, 2002, now abandoned.

(60) Provisional application No. 60/281,527, filed on Apr. 4, 2001.

(51) Int. Cl.
*C12N 5/071* (2010.01)
*A61K 35/36* (2015.01)
*C12M 1/33* (2006.01)
*C12M 1/00* (2006.01)

(52) U.S. Cl.
CPC .......... *C12M 45/06* (2013.01); *C12M 45/09* (2013.01); *C12M 45/22* (2013.01); *C12M 47/02* (2013.01); *C12N 5/0629* (2013.01); *A61M 2202/09* (2013.01); *A61M 2205/7545* (2013.01); *C12N 2500/98* (2013.01); *C12N 2500/99* (2013.01); *C12N 2509/00* (2013.01)

(58) Field of Classification Search
CPC ...... C12M 45/02; C12M 45/06; C12M 45/22; C12M 47/02; C12N 2500/98; C12N 2500/99; C12N 2509/00; C12N 5/0629
USPC ......................................................... 422/527
See application file for complete search history.

(56) References Cited

U.S. PATENT DOCUMENTS

| | | | |
|---|---|---|---|
| 3,647,632 A | | 3/1972 | Johnson et al. |
| 4,059,486 A | | 11/1977 | Tolbert |
| 4,254,226 A | | 3/1981 | Eisinger et al. |
| 4,304,866 A | | 12/1981 | Green et al. |
| 4,350,768 A | | 9/1982 | Tihon et al. |
| 4,418,691 A | | 12/1983 | Yannas et al. |
| 4,458,678 A | * | 7/1984 | Yannas .................. A61L 27/60 602/48 |
| 4,510,144 A | | 4/1985 | Hadden et al. |
| 4,533,635 A | | 8/1985 | Guédon et al. |
| 4,649,115 A | | 3/1987 | Safai et al. |
| 4,769,317 A | | 9/1988 | Hefton |
| 5,000,963 A | | 3/1991 | Hefton |
| 5,079,160 A | * | 1/1992 | Lacy ...................... C12M 45/09 435/1.1 |
| 5,292,655 A | | 3/1994 | Wille, Jr. |
| 5,328,695 A | | 7/1994 | Lucas et al. |
| 5,334,527 A | | 8/1994 | Brysk |
| 5,352,668 A | | 10/1994 | Burgeson et al. |
| 5,352,806 A | | 10/1994 | Gunawardana et al. |
| 5,441,539 A | * | 8/1995 | Alchas ..................... A61F 2/062 435/297.2 |
| 5,460,939 A | | 10/1995 | Hansbrough et al. |
| 5,507,385 A | * | 4/1996 | Koloski ................. B25H 3/023 206/372 |
| 5,556,783 A | | 9/1996 | Lavker et al. |
| 5,601,728 A | | 2/1997 | Kayal et al. |
| 5,624,638 A | * | 4/1997 | Negrotti ................. B01L 3/502 206/229 |
| 5,786,207 A | | 7/1998 | Katz et al. |
| 5,814,511 A | | 9/1998 | Chang et al. |
| 5,866,167 A | | 2/1999 | Van Bossuyt |
| 5,955,343 A | | 9/1999 | Holmes et al. |
| 5,994,129 A | * | 11/1999 | Armstrong ............. C12M 23/42 435/286.1 |
| 6,080,581 A | | 6/2000 | Anderson et al. |
| 6,207,451 B1 | | 3/2001 | Dennis et al. |
| 6,432,666 B1 | | 8/2002 | Hart |
| 7,655,465 B2 | | 2/2010 | Sherley et al. |
| 8,022,037 B2 | | 9/2011 | Li et al. |
| 2002/0106353 A1 | | 8/2002 | Wood et al. |
| 2007/0286880 A1 | | 12/2007 | Vasiliev et al. |
| 2010/0035815 A1 | | 2/2010 | Li et al. |
| 2010/0196334 A1 | | 8/2010 | Wood et al. |
| 2010/0255052 A1 | | 10/2010 | Young Anze et al. |
| 2011/0082082 A1 | | 4/2011 | Li et al. |

FOREIGN PATENT DOCUMENTS

| | | | |
|---|---|---|---|
| EP | 0 350 887 | | 1/1990 |
| EP | 0 444 270 | | 9/1991 |
| EP | 0751217 | | 5/1999 |
| WO | WO 90/00739 | * | 1/1990 |
| WO | WO 97/23602 | | 7/1997 |
| WO | WO 98/53850 | | 12/1998 |
| WO | WO 99/12555 | | 3/1999 |
| WO | WO 99/21963 | | 5/1999 |
| WO | WO 00/32207 | | 6/2000 |

OTHER PUBLICATIONS

Anonymous: "Clinical Cell Culture-Recell®" Internet Article, Online, Dec. 17, 2003, http://web.archive.org/web/20031217065921/http://www.clinicalcellculture.com/:80/one/02_04_recell.asp.

Anonymous, "Understanding Mesh Sizes," ESPI Metals, http://www.espimetals.com/index.php/online-catalog/334-understanding-mesh-sizes.

Antoni et al, "Development of the Total Care Unit." *ANZBA* (Queenstown) (1997) (Abstract).

Backman et al, "Scientific Visualisation as an Aide to Quantifying the Extent of Burn Injury." *ANZBA* (Gold Coast) (1995) (Abstract).

Barnden and Wood, "Adult Burn Patients Treated with a Combination of Skin Graft Techniques—What Dressing System to Use?" *ANZBA* (Gold Coast) (1995) (Abstract).

Barnden and Wood, "Designing a Tool to Facilitate and Standardise Burn Care in W. A." *ANZBA* (1996) (Abstract).

Barnden and Wood, "Dressings Used in the Burn Treated with Cultural Epidermal Autograft" *ANZBA* (Canberra) (1993) (Abstract).

Barrera, "The Use of Micrografts and Minigrafts for the Treatment of Burn Alopecia" *Plast. and Reconstr. Surg.* 103(2):581-584 (Feb. 1999).

Bird and Wood, "New Techniques of Managing Palmer Burns" *ANZBA* (May 1994) (Abstract).

Blennerhasset and Wood, "The Use of the Ultrasonic Aspiration as a Tissue Dissector for Excision of Burn Escar" *ANZBA* p. 40 (1996) (Abstract).

Booth and Wood, "Scar Assessment for the Future" *ANZBA* (Canberra) (1993) (Abstract).

Boyce, S.T., Ham, KG., "Cultivation, frozen storage and clonal growth of normal human epithelial keratinocytes in serum-free media." *J. Tissue Cult. Methods* 9:83-93 (1985).

Brandy, "A New Instrument for the Expedient Production of Minigrafts" *J. Dermatol. Surg. Oncol.* 18:487-492 (1992).

Caldow and Wood, "The Use of Self Adhesive Elastic Bandaging to Control Oedema in the Burn Injured Hand" *ANZBA* (Gold Coast) p. 35 (1995) (Abstract).

Cena et al, "Computerised Intergration of Multimodality Imaging in Scar Assessment." *ANZBA* (Gold Coast) p. 20 (1995) (Abstract).

Compton, "Wound Healing Potential of Cultured Epithelium" *Wounds* 5(2):97-111 (Mar./Apr. 1993).

Cooper et al., "The Effect of Aprotinin on Human Cultured Epidermal Cells" *PAN/Asian European Tissue Repair Society Wound Healing Meeting* (1997) (Abstract).

DeJong et al., "Pathways in Therapy for Burns Patients" *ANZBA* (Queenstown) (1997) (Abstract).

Deluca, M., et al., "Human Epithelial Cells Induce Human Melanocyte Growth In Vitro but Only Skin Keratinocytes Regulate Its Proper Differentiation in the Absence of Dermis," The Journal of Cell Biology, 107:1919-1926, (Nov. 1988).

Devalia et al., "Culture and comparison of human bronchial and nasal epithelial cells in vitro" *Resp. Med.* 84:303-312 (1990).

(56) References Cited

OTHER PUBLICATIONS

Ding and Han, "Recent Advances in Burn Wound Management in China" *Acta Chirurgiae Plasticae* 31 (2):84-91 (1989).
Dzubow, "Scar Revision by Punch-Graft Transplants" *J. Dermatol. Surg. Oncol.* 11(12):1200-1202 (Dec. 1985).
Early Burn Management Report. *PNAZBA* (1997) (Abstract).
Edgar and Wood, "Silicone Oil Revisited" *ANZBA* (Manly) PO-18:49 (1998) (Abstract).
Edgar et al., "Playing in a Team can be a Pain" *ANZBA* (Tasmania) p. 65 (1999) (Abstract).
Edgar et al., "The Good Oil?" *ANZBA* (Tasmania) p. 37 (1999) (Abstract).
Education—The Key to Better Management of the Burn Victim: An education project in Western Australia. Presentation. *Rural National Health Meeting* (1995) (Abstract).
Elliget and Lechner, "Human Bronchial Epithelial Cell Culture. Specialized Vertebrate Cultures" *Respir. Sys. Module* 13B3:1-17 (Abstract).
Falabella et al., "Surgical Combination Therapy for Vitiligo and Piebaldism" *Dermatol. Surg.* 21 :852-857 (1995).
Falabella, "Repigmentation of Leukoderma by Minigrafts of Normally Pigmented, Autologous Skin" *J. Dermatol. Sur. Oncol.* 4:916-919 (Dec. 1978).
Fong et al., "The Use of Clinical Indicators to Measure a Minimum Standard of Care for Early Burn Management" *ANZBA* (Queenstown) (1997).
Franklin et al., "Expansion of Bronchial Epithelial Cell Populations by In Vitro Culture of Explants from Dysplastic and Histologically Normal Sites" Am. *J. Respir Cell. Mol. Biol.* 15:297-304 (1996).
Gallico, III, M.D., et al., "Permanent Coverage of large Burn Wounds with Autologous Cultured Human Epithelium", The New England Journal of Medicine, vol. 31, No. 7, pp. 448-451, Aug. 16, 1984.
Gauthier and Surleve-Bazeille, "Autologous grafting with noncultured melanocytes: A simplified method for treatment of depigmented lesions" *J. Am. Acad. Dermatol.* 26(1:1):191-194 (1992).
Giele et al., "An alternative technique for the harvesting of cultured epithelial cell sheets" *Meth. Cell Sci.* 17:233-236 (1995).
Giele et al., "Anatomical Variations in Pressures Generated by Pressure Garments" *Plast. Reconstruct. Surg.* 101 (2):399-406 (Feb. 1998).
Giele et al., "Direct measurement of cutaneous pressures generated by pressure garments" *Burns* 23(2):137-141 (1997).
Giele et al., "Early Use of Pressure Masks to Avoid Facial Contracture During the Pregrafting Phase" *J. Burn Care Rehabil.* 16:641-645 (1995).
Giele et al., "Management of full thickness burns to lactating breasts" *Burns* 20(3):278-280 (1994).
Gospodarowicz and Greenburg, "The Role of Growth Factors and Extracellular Matrices in the Control of Mammalian Cell Proliferation" *The Biology of Normal Human Growth* (M. Ritzen et al., ed) Raven Press pp. 1-19 (1991).
Goulet et al., "Morphologic and Functional Properties of Bronchial Cells Isolated from Normal and Asthmatic Subjects" *Am. J. Respir. Cell. Mol. Biol.* 15:312-318 (1996).
Gramlich, G., "ReCell ein Erfahrungsbericht," Internet article, Online, Apr. 21, 2011, http://www.hagenmuehle.de/documents/MicrosoftWord-RecellVeroffentlichungInternet_000.pdf.
Griffiths and Wood, "The Influence of Geography on Burn Outcome" *ANZBA* (1994) (Abstract).
Griffiths and Wood, "The Use of Epidermal Derived Factors to Influence Wound Healing" *ANZBA* (Gold Coast) p. 11 (1995) (Abstract).
Griffiths et al., "Itch" *ANZBA* (Queenstown) (1997) (Abstract).
Guedon et al: "Culture and cytogenetic studies of adult human keratinocytes using a new growth factor", Differentiation, vol. 19, No. 2, 1981 (109-114).
Habberfield and Wood, "Burn Unit Support Groups—A Burning Issue" *ANZBA* (Canberra) p. 46 (1993) (Abstract).
Haberfeld and Wood, "Psychological Aspects of Burn Injury: Research Issues" *ANZBA* (Gold Coast) p. 67 (1995) (Abstract).
Haberfeld et al., "Psychological Reactions to Trauma: A Survey of Burns Unit Staff" *ANZBA* p. 42 (1996) (Abstract).
Hentzer and Kobayasi, "Suction Blister Transplantation for Leg Ulcers" *Acta Dermatovener* (Stockholm) 55:207-209 (1975).
Hirobe T. 1991, "Selective growth and serial passage of mouse melanocytes from neonatal epidermis in a medium supplemented with bovine pituitary extract," J Exp. Zool 257:184-194.
Hirobe: "Melanocyte stimulating hormone induces the differentiation of mouse epidermal melanocytes in serum-free culture", J. Cell. Phys., vol. 152, No. 2, Aug. 1992 (337-345).
Hornum and Wood, "Tragic Tales—Paediatric Burns in Motor Vehicles" *ANZBA* (1996) (Abstract).
Hornum and Wood, "Use of Retention Dressings in the Paediatric Population for Partial Thickness Burn Injury" *ANZBA* (May 1994) (Abstract).
Hornum et al., "The Impact of Integra™ Dermal Template Reconstruction on Paediatric Burn Care" *ANZBA* p. 82 (1999) (Abstract).
Hornum et al., "The Post Operative Management of Paediatric Burns Patients Treated with Cultured Epithelial Autograft in Fluid Suspension" *ANZBA* (Gold Coast) p. 18 (1995) (Abstract).
Humphrey, "Burns Education in Intensive Care" *ANZBA* PO-19:49 (1998) (Abstract).
Inayama et al., "In Vitro and In Vivo Growth and Differentiation of Clones of Tracheal Basal Cells" Am. *J. Pathol.* 134(3):539-549 (Mar. 1989).
Inayama et al., "The Differentiation Potential of Tracheal Basal Cells" *Lab. Invest.* 58(6):706-717 (1988).
Jensen, et al., "Cultivation at Low Temperature as a Measure to Prevent Contamination with Fibroblasts in Epithelial Cultures from Human Skin," The Journal of Investigative Dermatology, 77(2):210-212, (1981).
Jones and Elliget, "Method for the Culture of Human Bronchial Epithelial Cells from Tissues Obtained at Extended Postmortem Intervals" *Annual Meeting Abstracts* pp. 99 (Abstract).
Ke et al., "Cell Density Governs the Ability of Human Bronchial Epithelial Cells to Recognize Serum and Transforming Growth Factor Beta-1 as Squamous Differentiation-inducing Agents" Am. *J. Pathol.* 137(4):833-843 (1990).
Kisker-Biotech dry block heat and water baths product catalog, 3 pages, printed May 3, 2002.
Lechmere et al., "In Vitro Human Bronchial Epithelial Model Systems for Carcinogenesis Studies" In Vitro Models for Cancer Research. vol. VI Chapter 1 pp. 3-17.
Lechner et al., "Growth of Normal Adult Human Bronchial Epithelial Cells in a Serum-Free Medium" In Vitro 18(7):633-642 (Jul. 1982).
Lechner et al., "Induction of squamous differentiation of normal human bronchial epithelial cells by small amounts of serum" *Differentiation* 25:229-237 (1984).
Lee and Wood, "Management of Inhalation Injury" *ANZBA* (Manly) 0-34:39 (1998) (Abstract).
Lee et al., "An easy method for preparation of postage stamp autografts" *Burns* 26:741-749 (2000).
Liddiard et al., "Pressure Management of the Cultured Epithelial Autograft" *ANZBA* (Canberra) p. 38 (1993) (Abstract).
Liddiard et al., "Scar management of the Cultured Epithelial Autograft" *ANZBA* (Gold Coast) p. 37 (1995) (Abstract).
Liddiard et al., "The Direct Measurement of Cutaneous Pressure Generated by Pressure Garments" *International Symposium on Hypertrophic Scars* (Hong Kong) p. 36 (1995) (Abstract).
Lin et al., "Allogeneic microskin grafting of rabbits' skin wounds" *Burns* 19(3):208-214 (1993).
Lin et al., "Microskin grafting of rabbit skin wounds with Biobrane overlay" *Burns* 18(5):390-394 (1992).
Lucas, "Mini- and Micrografts Exclusively versus Standard Grafts Mixed with Mini- and Micrografts" p. 388 (1993) (Abstract).
Magnusson and Wood, "Epidemiological Differences of Burn Injuries in Aboriginal and Nonaboriginal Children" *ANZBA* (Tasmania) p. 77 (1999) (Abstract).
Magnusson et al., "The Effect of Skin Graft Storage on Keratinocytes" *ANZBA* (Manly) 0-33:39 (1998) (Abstract).

(56) References Cited

OTHER PUBLICATIONS

Magnusson et al., "The Proliferative Capacity of Keratinocytes Isolated from Skin Stored After Meshing vs Non-Meshed" *International Symposium on Hypertrophic Scars* (Hong Kong) p. 51 (1999) (Abstract).
Magnusson et al., "Transepidermal Water Loss as a Quantitative Method for Evaluating Epithelialisation" *ANZBA* (Tasmania) p. 31 (1999) (Abstract).
Magnusson et al., "Transepidermal Water Loss as a Quantitative Method for Evaluating Epithelialisation." Princess Margaret Hospital for Children *Res. Advances Seminar* p. 50 (1999) (Abstract).
Mardovin et al., "Micrografts: the "Super" Expansion Graft" *J. Burn Care Rehabil.* 13:556-559 (1992).
May et al., "Assessment of adhesion assays for use with keratinocytes" *Exp. Dermatol.* 10(1):62-69 (2001).
Mulekar, S., et al., "Treatment of vitiligo lesions by ReCell vs. conventional melanocyte-keratinocyte transplantation: a pilot study," The British Journal of Dermatology, 158(1):45-49, (Jan. 1, 2008).
Navarro F. A., et al., "Sprayed keratinocyte suspensions accelerate epidermal coverage in a porcine microwound model." *J. Burn Care Rehabil.* 21:513-518 (2000).
Neilson et al., "Case Presentation" *ANZBA* p. 71 (2000) (Abstract).
Nickoloff et al: "Further characterization of the keratinocyte somatomedin-C/insulin-like growth factor I receptor and the biological responsiveness of cultured keratinocytes to SM-C/IGF-I", Dermatologica, vol. 177, No. 5, 1988 (265-273).
Noel-Hudson et al: "Human epidermis reconstructed on synthetic membrane: influence of experimental conditions on terminal differentiation", In Vitro Cell. Dev. Biol., 1995, vol. 31, No. 7 (508-515).
Office Action in U.S. Appl. No. 10/068,299 dated Dec. 28, 2007.
Office Action in U.S. Appl. No. 10/068,299 dated Dec. 30, 2009.
Office Action in U.S. Appl. No. 10/068,299 dated Jul. 13, 2007.
Office Action in U.S. Appl. No. 10/068,299 dated Jul. 9, 2010.
Office Action in U.S. Appl. No. 10/068,299 dated Oct. 24, 2006.
Office Action in U.S. Appl. No. 10/068,299 dated Sep. 23, 2008.
Olsson and Juhlin, "Leucoderma treated by transplantation of a basal cell layer enriched suspension" *Brit. J. Dermatol.* 138:644-648 (1998).
Osborne et al: "Investigation into the biological stability of collagen/chondroitin-6-sulphate gels and their contraction by fibroblasts and keratinocytes: the effect of crosslinking agents and diamines", Biomaterials, vol. 20, No. 3, Feb. 1999 (283-290).
Papini and Wood, "Current concepts in the management of burns with inhalation injury" *Care Crit. Ill.* 15(2):61-66 (1999).
Papini et al., "Fluid Resuscitation Tissue Perfusion and Wound Salvage" *ANZBA* 0-30:37 (1998) (Abstract).
Papini et al., "Rapid Epithelial Cell Autograft" *ANZBA* (Manly) 0-31 :38 (1998) (Abstract).
Partial European Search Report in European Patent Application No. EP10184235 dated Apr. 27, 2011.
Perrot et al., "Heel Pain—Repercussions for Functional Outcome in Major Burns" *ANZBA* (Manly) 0-29:37 (1998) (Abstract).
Petersen et al: "Enhanced synthesis of collagenase by human keratinocytes cultures on type I or type IV collagen", *J. of Investigative Dermatology*, vol. 94, No. 3, Mar. 1990 (341-346).
Product No. 352070 of BD e-Catalog: Centrifuges and test tubes, 3 pages, printed May 3, 2002.
Product No. 352360 of BD e-Catalog: Centrifuges and test tubes, 2 pages, printed May 3, 2002.
Pye, "Cultured Keratinocytes as Biological Wound Dressings" (Abstract) (pp. 174-177).
Robinson and Wu, "Culture of Conducting Airway Epithelial Cells in Serum-Free Medium" *Tiss. Cult. Meth.* 13:95-102 (1991).
Savandra and Wood, "The Influence of Surgery on the Genetic Predisposition to Form Hypertrophic Scars in the Paediatric Scald Population" *ANZBA* (Manly) 0-32:38 (1998) (Abstract).
Shimizu et al., "Expression of "Cell-type-specific" Markers during Rat Tracheal Epithelial Regeneration" *Am. J. Respir. Cell Mol. Biol.* 7:30-41 (1992).
Silla et al., "Milton Solution: Does it have a place in burn treatment?" *ANZBA* p. 52 (2000) (Abstract).
Skinner and Wood, "A Possible Alternative to Custom made Pressure Garments for Scar Manipulation" *ANZBA* (May 1994) (Abstract).
Skinner and Wood, "The Clinical Use of Hydrophobic Fabric Garments in the Paediatric Population" *ANZBA* p. 34 (1996) (Abstract).
Skinner et al., "Sunburn—An Unnecessary Cause of Pain" *ANZBA* (Queenstown) (1997) (Abstract).
Skinner et al., "The Comparison of Pressure Garment Implementation &Removal from 1991-1994" *ANZBA* (Gold Coast) p. 36 (1995) (Abstract).
Skouge, "Techniques for Split-Thickness Skin Grafting" *J. Dermatol. Surg. Oncol.* 13(8):841-849 (Aug. 1987).
Smith and Wood, "Heterotopic Ossification in Burns: Conservative and Surgical Management" *ANZBA* (Canberra) p. 20 (1993) (Abstract).
Smithwick and Wood, "Have Changes in Attitude to the Use of Blood Products Impacted Upon Their Use with the Treatment of a Patient with Major Burn Injury" *ANZBA* (Queenstown) (1997) (Abstract).
Smithwick and Wood, "Self Harm" *ANZBA* (Perth) (2000) (Abstract).
Smithwick and Wood, "The Impact of Major Orthopaedic Injuries on Burn Nursing Care" *ANZBA* (Gold Coast) p. 33 (1995) (Abstract).
Smithwick and Wood, "The Impact of Religious Belief on the Management of the Burn Injury" Presentation (Abstract).
Smithwick et al., "Stress Management in the Burn Unit" *ANZBA* (Canberra) p. 27(1993) (Abstract).
Solotoft, "Treatment for Pitted Acne Scarring—Postauricular Punch Grafts followed by Dermabrasion" *J. Dermatol. Surg. Oncol.* 12 (10):1079-1084 (Oct. 1986).
Sperring and Wood, "Continuing to Care—Burn Management in the Outpatient Setting" *ANZBA* p. 29 (1996) (Abstract).
Stoner and Wood, "Cultured Epithelial Autograft Made Quick and Easy 1) Laboratory" *ANZBA* p. 41 (1996) (Abstract).
Stoner and Wood, "Systemic factors influencing the growth of cultured epithelial autograft" *Burns* 22(3): 197-199 (1996).
Stoner and Wood, "The Treatment of Hypopigmentation with Cultured Epithelial Cell" *ANZBA* (Gold Coast) p. 32 (1995) (Abstract).
Stoner and Wood, "Treatment of Burns to the Sole of the Foot with Site Specific Cultured Epithelial Autograft" *International Symposium on Hypertrophic Scars* (Hong Kong) p. 14 (1995) (Abstract).
Stoner and Wood, "Treatment of burns to the sole of the foot with site specific cultured epithelial autograft" Presentation at *The International Symposium on Hypertrophic Scar* (Hong Kong) pp. 1-7 (1995) (Abstract).
Stoner and Wood, "Treatment of Burns to the Sole of the Foot with Site Specific Cultured Epithelial Autograft" *ANZBA* (Gold Coast) p. 17 (1995) (Abstract).
Stoner and Wood, "When It Absolutely, Positively Has to Be There!—The Logistics of Long Distance Transport of Cultured Epithelial Autograft" *ANZBA* (Tasmania) p. 64 (1999) (Abstract).
Stoner and Wood, "Why Use Cultured Epithelial Autograft as a Suspension?" *ANZBA* 0-39:41 (1998) (Abstract).
Stoner and Wood, 'Take' of Cultured Epithelial Autograft Confirmed by the Presence of Cytokeratin 9 *The Surgical Res. Soc. Australasia Ann. Sci. Meeting* (Fremantle) (1997) (Abstract).
Stoner et al., "Cultured Airway Epithelium for the Treatment of Tracheal Burns" *PAN/Asian European Tissue Repair Society Wound Healing Meeting* (1997) (Abstract).
Stoner et al., "The Development of a Unique Technique of Cultured Epithelial Autograft Application" *The Surgical Res. Soc. Australasia Ann. Sci. Meeting* (Fremantle) (1997) (Abstract).
Stoner et al., "The Development of a Unique Technique of Cultured Epithelial Autograft Application" *ANZBA* (Queenstown) (1997) (Abstract).

(56) References Cited

OTHER PUBLICATIONS

Stoner et al., "The Treatment of Hypopigmented Lesions with Cultured Epithelial Autograft" *J. Burn Care Rehabil.* 21 (1):50-54 (2000).
Stoner et al., "The Use of Epithelial Cell Suspension with Meshed Split-Thickness Autograft Using Un-Cultured Keratinocytes in a Pig Model" *ANZBA* (Tasmania) p. 63 (1999) (Abstract).
Svensjö T., et al., "Autologous keratinocyte suspensions accelerate epidermal wound healing in pigs." *J. Surgical Res.* 99:211-221 (2001).
Tan et al., "The Management of Paediatric Palm Burn Injuries" *ANZBA* p. 65 (1996) (Abstract).
Teepe et al., "Fresh versus cryopreserved cultured allografts for the treatment of chronic skin ulcers" *Brit. J. Dermatol.* 122:81-89 (1990).
The current uses of cultured epidermis in Perth and its possible future. *Royal Australasian College of Surgeons*, Scientific Meeting (1992) (Abstract).
Vollberg et al., "Identification of Multiple Stages in the Program of Squamous Differentiation in Tracheobrochial Epithelial Cells" 1984.
Wheeland, "The Technique and Current Status of Pinch Grafting" *J. Dermatol. Surg. Oncol.* 13(8):873-880 (Aug. 1987).
Williams, "Intensive Care Burns—An Experience" *ANZBA* PL-5:23 (1998) (Abstract).
Wood and Caldow, "Advances in Burn Care Over 30 Years at Royal Perth Hospital" *ANZBA* p. 70 (1996) (Abstract).
Wood and Stoner, "Implication of basement membrane development on the underlying scar in partial-thickness burn injury" *Burns* 22(6):459-462 (1996).
Wood and Stoner, "The Clinical Use of Integra for Dermal Reconstruction" *Tissue Engineering Meeting* (Orlando) (1999) (Abstract).
Wood and Stoner, "The Implication of Basic Membrane Development on the Underlying Scar in Partial Thickness Burn Injury" *International Symposium on Hypertrophic Scars* (Hong Kong) p. 28 (1995) (Abstract).
Wood and Stoner, "The Use of Cultured Epithelial Autograft in Paediatric Burn Management" *European Club for Paediatric Burns.* Scientific Sessions (Zurich) (1996) (Abstract).
Wood and Stoner, "Western Australian Skin Culture Unit—A 5 Year Review" *Tissue Engineering Meeting* (Orlando) (1999) (Abstract).
Wood et al., "Augmented Clinical Assessment of Burn Injuries: Do You Believe What You See?" *ANZBA* (Queenstown) (1997) (Abstract).
Wood et al., "Current difficulties and the possible future directions in scar assessment" *Burns* 22(6):455-458 (1996).
Wood et al., "Scar management of cultured epithelial autograft" *Burns* 22(6):451-454 (1996).
Wood et al., "Scar Management of the Cultured Epithelial Autograft" *International Symposium on Hypertrophic Scars* (Hong Kong) p. 19 (1995) (Abstract).
Wood et al., "The Current Difficulties and the possible future direction in scar assessment" *International Symposium on Hypertrophic Scars* (Hong Kong) p. 20 (1995) (Abstract).
Wood et al., "The Role of Integra Dermal Template in Scar Reconstruction Post Burn Injury" *ANZBA* (Tasmania) p. 79 (1999) (Abstract).
Wood et al., "Wound Bed Preparation with Dermal Preservation" *ANZBA* (1996) (Abstract).
Wood, "Advances in the use of cultured skin in wound care" *Second Australian Wound Management Association* (1998) (Abstract).
Wood, "Clinical Indications for the Use of Integra" *ANZBA* (1997) (Abstract).
Wood, "Dermal reconstruction in the repair of full thickness skin loss" *The Second Australian Wound Management Association Conference* (Queensland) (1998) (Abstract).
Wood, "Dermal Replacement for Use with Cultured Epidermal Autograft" *ANZBA* (Canberra) p. 36 (1993) (Abstract).
Wood, "Early Burn Excision" Oral Presentation. *Indonesian Surgeons Association Congress* pp. 1-4 (Jul. 1996) (Abstract).
Wood, "Experience of the First Two Years of the Skin Culture Laboratory in Western Australia" *ANZBA* (Gold Coast) p. 10 (1995) (Abstract).
Wood, "Facial Burn Management" *ANZBA* (Queenstown) (1997) (Abstract).
Wood, "Facial Burn Management" *PAN/Asian European Tissue Repair Society Wound Healing Meeting* (1997) (Abstract).
Wood, "Integra 12 Months On." *ANZBA* (Manly) 0-38 (1998) (Abstract).
Wood, "Long distance wound care" *Second Australian Wound Management Association* (1998) (Abstract).
Wood, "Major Burns Disaster Plan" *ANZBA* (Tasmania) p. 66 (1999) (Abstract).
Wood, "Quality assurance in burn patient care: the James Laing Memorial Essay, 1994" *Burns* 21 (8):563-568 (1995).
Wood, "Skin Grafting to Achieve Minimal Scarring" *ANZBA* (Canberra) p. 40 (1993) (Abstract).
Wood, "Tailored Wound Healing" *ANZBA* (Tasmania).p. 30 (1999) (Abstract).
Wood, "Teamwork" *ANZBA* (Manly) PL-6:23 (1998) (Abstract).
Wood, "The Clinical Indications for the Use of Cultured Epithelial Autografts" Oral Presentation at the *Indonesian Surgeons Association Congress* p. 1-4 (Jul. 1996) (Abstract).
Wood, "The Ethics of Burn Care" *ANZBA* (Manly) 0-36-38:40 (1998) (Abstract).
Wood, "The First Four Years of the Skin Culture Laboratory in W.A." *The Surgical Res. Soc. Australasia Ann. Sci. Meeting* (Fremantle) (1997) (Abstract).
Wood, "The Use of Tissue Culture Techniques for the Treatment of the Partial Thickness Burn Injury" *Primary Intent.* (Australia) 1(1):16-17 (Nov. 1993).
Wright and Wood, "The Use of Intranasal Fentanyl PCA for Pain Control During Burn Wound Dressing Change" *ANZBA* p. 60 (1996) (Abstract).
Wu and Stoner, "Cultured Epithelial Autograft Made Quick and Easy 2) Surgery" ANZBA p. 42 (1996) (Abstract).
Wu et al., "Growth and differentiation of human nasal epithelial cells in culture. Serum-free, hormone-supplemented medium and proteoglycan synthesis" *Am. Rev. Resp. Dis.* 132(2):311-320 (1985) (Abstract).
Wyle and Wood, "Sensation Following Integra Dermal Replacement of Full Thickness Burns" *ANZBA* (Tasmania) p. 83 (1999) (Abstract).
Young, A., et al., "Human Melanocytes and Keratinocytes Exposed to UVB or UVA In Vivo Show Comparable Levels of Thymine Dimers," The Journal of Investigative Dermatology, 11(6):936-940, (Dec. 1998).
Zhang et al., "Microskin Grafting in the Treatment of Extensive Burns: A Preliminary Report" *J. Trauma* 28(6):804-807 (1988).
Zhang et al., "Microskin grafting. I. Animal experiments" *Burns* 12(8):540-543 (1986).
Zhang et al., "Microskin grafting. II. Clinical report" *Burns* 12(8):544-548 (1986).
Office Action in U.S. Appl. No. 13/223,577 dated Jan. 11, 2012.
Office Action in U.S. Appl. No. 13/223,577 dated Oct. 22, 2012.
Office Action in U.S. Appl. No. 13/223,577 dated Dec. 19, 2013.
Office Action in U.S. Appl. No. 13/223,577 dated Sep. 24, 2014.
Office Action in U.S. Appl. No. 13/036,569 dated Oct. 11, 2011.
Office Action in U.S. Appl. No. 13/036,569 dated Mar. 9, 2012.
Office Action in U.S. Appl. No. 13/036,569 dated Dec. 21, 2012.
Office Action in U.S. Appl. No. 13/036,569 dated Oct. 10, 2013.
Office Action in U.S. Appl. No. 12/699,554 dated Apr. 10, 2012.
Office Action in U.S. Appl. No. 12/699,554 dated Dec. 31, 2012.
Office Action in U.S. Appl. No. 12/699,554 dated Feb. 24, 2014.
EPO Decision to Grant dated Nov. 27, 2014.
EPO Office Action dated Sep. 12, 2014.
Fulda, et al. "Cellular Stress Responses: Cell Survival and Cell Death." International Journal of Cell Biology; vol. 2010; Article ID 214074; pp. 1-23; (2010).
Cheng, Chieh-Fang et al., "A fragment of secreted Hsp90a carries properties that enable it to accelerate effectively both acute and diabetic wound healing in mice." The Journal of Clinical Investigation; vol. 121, No. 11; pp. 4348-4361; Nov. 2011.

(56) References Cited

OTHER PUBLICATIONS

Lindquist, et al. "The Heat-Shock Proteins"; Annu. Rev. Genet. 1988. 22:631-77.
Ben-Porath, Ittai et al.; "When cells get stressed: and integrative view of cellular senescence"; The Journal of Clinical Investigation; vol. 113; No. 1; pp. 8-13; Jan. 2004.

* cited by examiner

CELL SUSPENSION PREPARATION TECHNIQUE AND DEVICE

CROSS REFERENCE TO RELATED APPLICATIONS

The present application is a continuation of U.S. patent application Ser. No. 13/223,577, filed Sep. 1, 2011, which is a divisional application of U.S. patent application Ser. No. 13/036,569, filed Feb. 28, 2011, which is a continuation of U.S. patent application Ser. No. 10/068,299, filed Feb. 6, 2002, which claims priority to and the benefit of Australian Provisional Patent Application PR2989, filed Feb. 7, 2001 and U.S. Provisional Patent Application No. 60/281,527, filed Apr. 4, 2001, the disclosures of all of which are incorporated herein by reference in their entirety.

FIELD OF THE INVENTION

This invention relates to a simple, rapid and cost effective technique for grafting of cells, and in particular to a device for preparing a suspension of cells from a tissue sample obtained from a donor site and applying that suspension of cells to a recipient site.

BACKGROUND ART

There are many methods of treating wounds known to those skilled in the art. For example, skin grafting techniques exist which aim to reconstruct the skin covering areas of the body where there is either damage or defects to the skin. In general, these types of grafts are classified according to their host-donor relationship and by their thickness. The most clinically applied graft is the autologous graft, whereby tissue is taken from one area of the body and applied to another area. The grafted tissue then develops a new blood supply and attaches to the underlying tissues.

There are several types of skin grafts presently used, including split-thickness, full-thickness grafts, and micro-grafting. Each of these graft types must be prepared using certain techniques, and each one has its inherent advantages and disadvantages. Split-thickness grafts often require considerable skill, time and expensive equipment to perform. Further, donor sites are painful, result in scarring and limit the area able to be covered. Although they may be more successful than full-thickness grafts, they are usually less cosmetically attractive. Full-thickness grafts require less skill or expensive equipment, and their cosmetic appearance is better than that of split-thickness grafts. However, full-thickness grafts do not "take" as well as split-thickness grafts. Micro-grafts are more easily accomplished and require no special instruments. However, their cosmetic appearance is not as good as other techniques, as the resulting scarring is unacceptable.

A variation to the above grafting techniques is the mesh graft, which is a type of split-thickness or full-thickness skin graft in which parallel rows of slits are cut in the tissue being treated. Some of the advantages of mesh grafts include: a greater coverage of the effected area, drainage of blood or serum from under the graft, and increased conformity of the graft to uneven recipient areas. This technique has been very successful, with 90 to 100 percent "take" when the grafts have been applied on healthy granulation beds.

An alternative to split-skin grafting is to form a blister under suction at a donor site and transplant to the recipient site. The production of blisters to treat wounds has been used since the 1960s. The blisters are produced by a suction device, such as Dermavac™, at a suction pressure of approximately 250-300 mmHg for 1-2 hours. The blisters are then cut off and placed on the wound. The healing time is around 10-14 days. There are several disadvantages of this method such as the amount of time required to prepare the graft is too long and the graft may not result in re-pigmentation of the area; or uneven pigmentation is common around the edges of the area of treatment.

Micro-grafting has become a more common approach for large area cover and involves the "snipping off" of a number of very small sections of tissue from a donor site and applying then to a dressing, which is in turn applied to the wound area.

The most advanced technology for the generation of a tissue in vitro is to culture epidermis. Cultured epithelial autografts (CEA) are an important adjunct in the coverage of burns and other situations in which large areas of the body's surface experience skin loss. There are many centers throughout the world with tissue culture facilities whose aim is to produce autologous epithelial grafts for use in a wide variety of applications. The usefulness and application of CEA is related to its ability to achieve confluent cells sheets suitable for grafting. This technique overcomes many of the disadvantages of the previous treatments described above. For example, cultured epithelial autografts reduce the demand for donor sites. However, these autografts are slow growing and require time for culturing of the grafts, which often exceeds the time of preparation of the recipient's sites.

The present invention provides a cellular suspension together with a method for preparing that suspension and a device for its preparation each of which seek to ameliorate one or more of the disadvantages associated with prior art grafting technology.

SUMMARY OF THE INVENTION

The subject invention relates to a unique cell suspension and method for its preparation that is rapid, efficient and simple to prepare and apply. It also relates to a method for treating a patient using the unique cell suspension and to an apparatus suitable for use in the method preparation. Use of the described device while not essential for practicing the method of the invention has been found to significantly reduce the complexity associated with the use of conventional grafting technology such as CEA.

According to a first aspect of the invention there is provided a method for preparing a cell suspension suitable for application to a patient, which method comprises the steps of:

(a) subjecting a tissue sample including cells suitable for grafting to a patient, to at least a physical and or chemical dissociating means capable of dissociating cellular stratum in the tissue sample;

(b) removing the tissue sample from the presence of the tissue dissociating means used in step (a) and harvesting in the presence of a nutrient solution cells from the tissue sample, cells suitable for grafting on to a patient wherein the nutrient solution is (i) free of xenogenic serum, (ii) capable of maintaining the viability of the cells until applied to a patient and (iii) is suitable for direct application to a region on a patient undergoing tissue grafting; and (c) filtering the cellular suspension produced according to step (b) to remove large cellular conglomerates.

In a preferred form of the invention the dissociating means is of a chemical nature such as an enzyme which is capable of disrupting cellular bonding like for example trypsin. Further, preferably the filtered cellular suspension is diluted to an appropriate cell density using a nutrient solution, which may be anything from a basic salt solution to a more complex nutrient solution.

According to a second aspect of the invention there is provided a cell suspension produced according to the above method. Preferably the cells in the suspension are autologous cells (i.e. they are isolated from the patient requiring an autograft). The inventors have observed that by removing xenogenic serum from the cell suspension there is less likelihood of transmission of infection and xenogenic reactions between a patient and the serum are eliminated. Another feature of the cell suspension produced according to the above method is that the tissue sample used to isolate the cells in the suspension is removed from the enzyme solution before the cells are harvested. When cells are exposed to enzymes capable of damaging inter-cellular adhesion the viability of the cellular suspension decreases over time thereby reducing the efficiency of the grafting when applied to a patient. The cell suspension produced according to the above method has been observed to possess greater cellular viability compared to comparative methods that harvest the cells at regular intervals whilst the tissue is immersed in the presence of enzymes like trypsin.

According to a third aspect of the invention there is provided a method of treating a patient in need of graft surgery, said method comprising the steps of:

(a) preparing a cell suspension according to the above method;

(b) administering the suspension directly to a region on the patient that requires a cell graft in a manner that facilitates spreading of the cell suspension in a relatively even distribution over the graft region.

In an alternate form, the invention consists in the use of a cellular suspension suitable for grafts, which suspension is prepared according to the following steps:

(a) subjecting a tissue sample including cells suitable for grafting to a patient, to an enzyme suitable for dissociating cohesive pieces of the tissue stratum in the sample;

(b) removing the sample from the enzyme solution used in step (a) and harvesting in the presence of a nutrient solution cells from the tissue sample, which cells are suitable for grafting on to a patient wherein the nutrient solution is (i) free of xenogenic serum, (ii) capable of maintaining the viability of the cells until applied to a patient and (iii) is suitable for direct application to a region on a patient undergoing tissue grafting;

(c) filtering the cellular suspension produced according to step (b) to remove large cellular conglomerates;

for the preparation of medicament suitable for the treatment of tissue disorders requiring grafting.

According to a fourth aspect of the invention there is provided an apparatus for developing a tissue regeneration solution, said apparatus comprising:

(a) a heating means suitable for heating an enzyme solution to a required temperature and which is capable of maintaining that solution at the desired temperature for a suitable amount of time; and (b) a filter recess comprising a filter means capable of separating large cellular congregates from a cellular suspension.

When the enzyme solution is placed in contact with the heating means it is preferably heated in a manner that avoids localized heating within the solution.

Other aspects and advantages of the invention will become apparent to those skilled in the art from a review of the ensuing description, which proceeds with reference to the following illustrative drawings.

DETAILED DESCRIPTION OF THE INVENTION

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and where appropriate methods are clearly within the scope of the invention as described herein.

Throughout this specification and the claims that follow, unless the context requires otherwise, the word "comprise", or variations such as "comprises" or "comprising", will be understood to imply the inclusion of a stated integer or group of integers but not the exclusion of any other integer or group of integers.

Having regard to the above, this invention provides a unique method and or device suitable for producing a transplantable cellular suspension of living tissue suitable for grafting to a patient. In applying the method and/or in using the device donor tissue is harvested, subjected to a tissue dissociating means, cells suitable for grafting back to a patient are collected and dispersed in a solution that is suitable for immediate dispersion over the recipient graft site.

The subject invention has many advantages over the prior art some of which are illustrated in the following paragraphs.

1. It provides a time efficient method for supplying a cellular cover to a tissue in a clinical setting. That is, cells are available when needed at the time of surgery. This is achievable because there is a very short preparation period of the cells, thus allowing grafting to be performed perioperatively or in the rooms of a specialist physician or General Practitioner.

2. It provides a method and an apparatus which significantly reduces the complexity associated with the use of conventional CEA's and is particularly useful in cases of burn injury that have presented late. In some instances, cells are unavailable at the time of surgery, either due to delayed referral of a patient with an unhealed burn or simply because the time needed for culturing of the grafts had exceeded that for preparation of the recipient would bed. The present invention ameliorates the issue of graft preparation time.

3. It aids in the achievement of rapid cell coverage in areas of injury and donor sites. It provides a means for reducing the size of donor sites—the biopsy donor site is markedly smaller than a split skin graft donor site and reduces or eliminates the use of split skin graft donor sites; improves expansion rate of cell coverage; improves the rate of healing of small burns; is useful for small areas of skin reconstructions, such as scars; and improves scar quality.

4. It ameliorates problems associated with the use of solutions used during conventional tissue culture process. According to the method of preparation and treatment the cells used in a graft are suspended in a nutrient solution free of xenogenic serum. That suspension is then placed directly onto the recipient site.

5. It provides a means for the treatment of various skin disorders or diseases. For example, it may be used for the following: epidermal resurfacing, replacement after skin loss, site match-up during re-pigmentation of an area of skin, treatment of burn wounds, leukoderma, vitiligo, piebaldism, in the treatment of scars—for example, caused through incorrect wound healing, improper scar direction or scar distortion from wound contraction, acne scars; resurfacing cosmetic dermabrasion, resurfacing after laser treatment and in association with dermal reconstruction. Additionally the method may be used for cell replacement therapy, including, for example, nerve cell replacement treatment, epithelial cell (such as urothelial cell, buccal mucosal cell and respiratory epithelial cell) replacement treatment, endothelial cell replacement treatment and osteogenic precursor cell replacement treatment.

6. It provides a means to produce a suspension of cells in a ratio to each other comparable with those seen in situ. That is, due to the manner of preparation of the cellular suspension, cells such as keratinocyte basal cells, Langerhans cells, fibroblasts and melanocytes typically have enhanced survival rates in comparison to standard tissue culture techniques, whereby selective cell culture can result in the loss of certain cell types. This has the advantage of allowing for the correct re-pigmentation of skin after a skin graft.

7. It allows faster surgery and healing—thereby reducing trauma for patients during the phase of their medical care.

According to the first aspect of the invention there is provided a method for preparing a cell suspension suitable for use in resurfacing and regeneration of damaged tissue.

According to this method, tissue (preferably of an autologous nature) is harvested from a patient by means known in the art of tissue grafting. Preferably this is achieved by taking a tissue biopsy. With the harvesting of the biopsy consideration must be given to the depth of the biopsy and the surface area size. The depth and size of the biopsy influence the ease at which the procedure can be undertaken and speed with which a patient recovers from the procedure. In a highly preferred form of the invention the donor site should be chosen to appropriately match the recipient site, for example post-auricular for head and neck, thigh for lower limbs, inner-upper-arm for upper limbs, or palm for sole or vice-versa.

Once a biopsy has been harvested from a patient the tissue sample is subjected to physical and/or chemical dissociating means capable of dissociating cellular stratum in the tissue sample.

Methods for dissociating cellular layers within the tissues are well known in the field. For example, the dissociating means may be either a physical or a chemical disruption means. Physical dissociation means might include, for example, scraping the tissue sample with a scalpel, mincing the tissue, physically cutting the layers apart, or perfusing the tissue. Chemical dissociation means might include, for example, digestion with enzymes such as trypsin, dispase, collagenase, trypsin-EDTA, thermolysin, pronase, hyaluronidase, elastase, papain and pancreatin. Non-enzymatic solutions for the dissociation of tissue can also be used.

Preferably, dissociation of the tissue sample is achieved by placing the sample in a pre-warmed enzyme solution containing an amount of enzyme sufficient to dissociate cellular stratum in the tissue sample. This may be achieved, for example using a trypsin solution, however, any other enzyme such as dispase, collagenase, trypsin-EDTA, thermolysin, pronase, hyaluronidase, pancreatin, elastase and papain that cause cells to become detached from other cells or from solid surfaces may be used for this purpose. When the enzyme used is trypsin the enzyme solution used in the method is preferably calcium and magnesium free. One such solution is preferably calcium and magnesium ion free phosphate buffered saline.

Where the tissue biopsy is derived from a patient's skin (comprising epithelial-dermal cells) the amount of trypsin that might be used in the method is preferably between about 5 and 0.1% trypsin per volume of solution. Desirable the trypsin concentration of the solution is about 2.5 to 0.25%, with about 0.5% trypsin being most preferred.

The time period over which the tissue sample is subjected to the trypsin solution may vary depending on the size of the biopsy sample taken. Preferably the tissue sample is placed in the presence of the trypsin solution for sufficient time to weaken the cohesive bonding between the tissue stratum. For example, where the tissue sample is taken from a patient's skin the sample might be placed in trypsin for a 5 to 60 minute period. Preferably, the tissue sample is immersed in the trypsin solution for between 10 and 30 minutes with 15 to 20 minutes being optimal for most tissue samples.

After the tissue sample has been immersed in the trypsin solution for an appropriate amount of time, the sample is removed from the trypsin and washed with nutrient solution. Washing the tissue sample may involve either partial or complete immersion of the treated sample in the nutrient solution. Alternatively, and more preferably, the wash solution is dripped on the tissue sample in sufficient volume to remove and or significantly dilute any excess trypsin solution from the surface of the sample. Preferably any dilution that might occur would lead to less than 0.05% trypsin in the nutrient solution.

The nutrient solution used in the method should be capable of significantly reducing and more preferably removing the effect of the trypsin either by dilution or neutralization. The nutrient solution used in the method will also preferably have the characteristics of being (i) free of at least xenogenic serum, (ii) capable of maintaining the viability of the cells until applied to a patient, and (iii) suitable for direct application to a region on a patient undergoing tissue grafting. The solution may be anything from a basic salt solution to a more complex nutrient solution. Preferably, the nutrient solution is free of all serum but contains various salts that resemble the substances found in body fluids; this type of solution is often called physiological saline. Phosphate or other non-toxic substances may also buffer the solution in order to maintain the pH at approximately physiological levels. A suitable nutrient solution that is particularly preferred is Hartmann's solution.

After application of the nutrient solution to the tissue sample, the cellular stratum of the sample are separated permitting cells capable of reproduction to be removed from the cellular material and suspended in the nutrient solution.

Where the tissue sample is skin the dermis and epidermis are preferably separated to allow access to the dermal-epithelial junction of both surfaces.

Cells capable of reproduction are then removed from the separated stratum by any means known in the art. Preferably, the reproductive cells are scraped off the surface of the stratum using an instrument such as a scalpel. Cells capable of reproduction within the dermal-epithelial junction include but are not limited to keratinocyte basal cells, Langerhans cells, fibroblasts and melanocytes. Following release of the cells from the tissue sample they are suspended in the nutrient solution. Preferably only a small volume of nutrient solution is applied to the tissue sample during this harvesting step otherwise the suspension may become too fluid therein providing difficulties in applying the suspension to the graft.

To avoid excessively large cellular congregates in the cellular suspension the suspension is preferably filtered. Any filter capable of separating excessively large cellular congregates from the suspension may be used in this preferred step of the invention. In a highly preferred form of the invention the filter size is between 50 µm and 200 µm. More preferably it is between 75 µm and 150 µm, with 100 µm being one specific example.

Prior to application to the graft site or immediately after filtering, the cellular suspension may be diluted to produce an appropriate cell density suitable for the purpose to which the suspension is to be used.

According to the second aspect of the invention there is provided an aqueous cell suspension produced by the method described in the first aspect of the invention. The cell suspension provided by this method is highly suitable for tissue regeneration and grafting techniques. An important advantage of utilizing such a suspension in grafting technology is that it can be used to greatly expand the area or volume of a wound that can be treated quickly by in situ multiplication of a limited number of cells. The number and concentration of cells seeded onto graft site may be varied by modifying the concentration of cells in suspension, or by modifying the quantity of suspension that is distributed onto a given area or volume of the graft site.

By suspending cells in a nutrient solution which is at least (i) free of xenogenic serum, (ii) capable of maintaining the viability of the cells until applied to a patient and (iii) is suitable for direct application to a region on a patient undergoing tissue grafting, the inventors have found that the outcome of patient grafts is improved. A partial explanation for this appears to be attributable to the removal of xenogenic serum and more preferably all serum from the cell suspension. Xenogenic serum is a common additive in grafting culture medium and is well known to cause potential infective and hypersensitivity problems. Such serum is however generally required for the in vitro expansion of the cells and to neutralize the action of the enzyme if the enzyme used is trypsin. The nutrient solution used in the present invention does not require such serum because the cell population within the suspension is not expanded prior to application to the graft site. Rather cellular multiplication is encouraged on the patient rather than in an in vitro system. When trypsin is used neutralization is achieved by other means.

Another unique feature of the cell suspension produced according to the method of the first aspect of the invention is that the composition of cells in the cellular preparation is comparable to that seen in situ compared to prior art cellular preparation. One possible explanation for this is that in the prior art, culture of the cellular preparation utilizes selective culture for keratinocytes, therefore loss of cellular constituents such as fibroblasts and melanocytes occurs whereas the cellular suspension produced from the first aspect of the invention has a cell composition comparable to the in situ cell population. Another feature of the cellular suspension produced from the first aspect of the invention is that the graft cells are more viable as they are harvested in a nutrient solution as distinct from prior art cell harvesting procedures which utilize techniques where the cells are harvested whilst exposed to powerful digestive enzymes for excessive periods of time. When the cells are exposed to such enzymes for excessive periods of time the viability of the cellular suspension decreases.

According to the third aspect of the invention there is provided a method of treatment of the patient requiring a tissue graft. By this method the cellular suspension produced according to the first aspect of the invention is applied to a graft site. A liquid suspension containing cells may be manually distributed onto the graft site by any of several techniques, which include spraying, spreading, pipetting and painting.

In a highly preferred form of the invention the suspension is sprayed on to a graft site. The suspension may be sprayed through any type of nozzle that transforms liquid into small airborne droplets. This embodiment is subject to two constraints. First, it must not subject the cells in solution to shearing forces or pressures that would damage or kill substantial numbers of cells. Second, it should not require that the cellular suspension be mixed with a propellant fluid that is toxic or detrimental to cells or wound beds. A variety of nozzles that are commonly available satisfy both constraints. Such nozzles may be connected in any conventional way to a reservoir that contains the cellular suspension.

Alternatively the suspension may be delivered via a pipette, common "eye-droppers," syringe and needle and or other similar devices to place small quantities of cellular suspension on a graft site.

After the cell suspension has been applied to the recipient graft site, the wound may be dressed with a wound dressing. In a preferred embodiment the dressing is Surfasoft™ a woven nylon dressing. Preferably, the healing of the wound is followed up by standard protocols for skin graft treatment known to those skilled in the art.

According to the fourth aspect of the invention there is provided an apparatus for developing a tissue regeneration solution, which has a heating means suitable for heating an enzyme solution to a required temperature and which is capable of maintaining that solution at the desired temperature for a suitable amount of time; and a filter recess comprising a filter means capable of separating large cellular congregates from a cellular suspension.

In a preferred form of the fourth aspect of the invention the apparatus also includes a reservoir capable of holding a tissue sample and a nutrient solution which solution is also capable of maintaining the viability of the cells in the tissue sample. More preferably the reservoir is of sufficient size to permit manipulation of the tissue sample permitting separation of the tissue cellular stratum and harvesting of those cells from the stratum suitable for grafting.

The apparatus may also include one or more fluid containment wells for storage of fluids such as the nutrient solution. The wells may alternatively serve as a receptacle for a container such as a plastic or glass vial that holds the nutrient solution. Preferably, the well is capable of holding at least a 10 ml volume. Such wells permit ease of fluid application to the tissue sample. Storage of such fluids in close proximity to its site of application also provides the advantage of reducing the risk of accidental leakage of the fluid and provides an easy means for accessing the fluid for accurately delivering it to either the tissue sample or the cell suspension.

In a highly preferred form of the invention the apparatus comprises a first and second member wherein:

(1) the first member includes:

(a) at least a heating means suitable for heating an enzyme solution to a required temperature and which is capable of maintaining that solution at the desired temperature for a suitable amount of time;

(b) at least a filter recess comprising a filter means capable of separating large cellular congregates from a cellular suspension;

(c) at least a fluid containment well for storage of nutrient solution;

(2) the second member forms a reservoir capable of withholding a tissue sample and nutrient solution in fluid containment; and wherein the first member provides a seat upon which the second member may be placed during manipulation of the tissue.

In a further preferred form of the invention the first member provides an storage compartment into which tools and solutions used in the above described method may be stored. Where such a compartment is provided in the apparatus the second member may provide the lid or closure to that compartment. In use the lid is preferably removed from the top of the compartment and inverted. The underside of the lid preferably forms the reservoir therein enabling the second member to serve a dual purpose. Tools and solutions used in the method can be accessed from the compartment. The inverted lid may then be seated back over the compartment therein providing the reservoir for the apparatus.

The apparatus may be made from metal, plastic or any other material. Further, the container may be any size. Preferably the size of the container is only limited by its intended use and the need for sterilization such as by the use of gamma irradiation and or ethylene oxide.

It should be appreciated that the heating means employed in the apparatus may simply constitute a heating pad or pads on the top of the first member. There are however, attendant problems with such arrangements, not least of which is the possibility of accidental spillage of the container undergoing heating. Therefore, in an embodiment, one or more heating means may be housed within a recess in the first member. Also located within that recess is at least a container into which tissue may be placed for exposure to the enzyme solution. In an alternate embodiment one or more heating means may be housed in the base of the apparatus. In such a configuration the first member contains at least an opening suitable for receiving a container capable of holding fluid, which opening provides access for the container to the heating means.

It will be appreciated that if the apparatus is designed for more than one use the heating means may be capable of being repeatedly heated and cooled. Alternatively each heating unit may be capable of a single use, but multiple heating units may be provided with the apparatus to facilitate multiple heating events.

In a highly preferred configuration of the apparatus a heating collar is located within a recess therein forming a heating recess in the first member within which there is located a container (e.g., a vial) for the enzyme. The container is preferably held in place by at least a restraining means, which desirably surrounds part of the upper portion of the container preventing accidental release of the container from the apparatus. In circumstances, where the apparatus is intended for single use the restraining means may be formed as an integral part of the first member, thus meaning that removal of the container may only be achieved by physically breaking the first member.

The heating means used in the apparatus is preferably controlled by circuitry permitting activation of the heating element when required. For example the heating means may be switched on by depressing the start button located, for example, on the surface of the first member. Alternately the heating means may be activated by pushing the container down with sufficient force to activate a switch located in the base of the apparatus. A person of ordinary skill in the field will appreciate that a wide range of electronic means may be used to activate the heating unit provided in the apparatus.

Desirably the heating unit is also operably linked to a timer mechanism, which is adapted to heat the enzyme solution for a pre-defined period of time. In circumstances where the apparatus is intended for multiple uses, preferably the timer can be set to deactivate the heating element when a particular amount of time is reached. At which point an alarm may activate to inform the user that the time is up. The alarm may be audible or in the form of a light display.

In a further preferred embodiment of the present invention the heating means may be provided with an adjustable temperature control. Where temperature adjustment is required such variation may be achieved by adapting the heating control circuitry to include or communicate with a temperature control mechanism permitting the temperature of the heating unit to be constantly varied within a constant range, or it may present a range of select temperatures that the heating control means can be set at. A temperature control means will beneficially be included in the apparatus where the apparatus is to be used in the harvesting and preparation of different cell types and or where different enzymes are used in the harvesting method for which the apparatus has unique application.

In an alternate more preferred form, the apparatus is designed for single use. In such instances the timer mechanism is part of the circuitry that controls the heating means. Once the heating means has been activated it heats the solution for a predefined period of time and then self-destructs. It should be appreciated by those skilled in the art that such an the apparatus may be fitted with various monitoring means that are capable of indicating such things as: the enzyme has reached the required temperature; the amount of time that the enzyme has been in the solution for; and or the amount of time left before the circuitry self-destructs etc. By way of example only, the monitoring means might consist of a series of LED's that activate when certain events occur. In a highly preferred embodiment the heating element preferably remains in the heating mode for a maximum of 45 minutes to 1 hour.

The heating means may be powered by any means known in the art. Preferably, the power supply is provided by battery/batteries. In one form of the invention, the power supply is a battery or a plurality of batteries located in the base of the apparatus.

In a further embodiment of the invention the apparatus may be provided with one or more means to facilitate mixing of the solutions used in the invention, such as for example an enzyme solution. In this respect, and by way of example only, the apparatus may include a means for vortexing the solution; such as an electromagnetic system that is adapted to agitate a magnetic bead. Where the apparatus includes an electromagnetic mixing system the magnetic bead is preferably provided in the container (e.g., vial) in which the solution is stored in the apparatus. Alternatively the magnetic bead may be added to the solution when mixing is desired.

In a highly preferred form of the invention the mixing means is combined with the heating means either as a single unit or as separate units to facilitate constant heating of the solution in an even manner. Using such a mixing means avoids the possible overheating of solution closest to the heating unit while the solution is heated. Such a system will provide a more constant heating of the solution. Alternate means for mixing the solution will be known in the art and include, mechanical, physical, electrical and electromagnetic means as an example. While any mixing means may be employed in the apparatus, preferably the mixing means is either selected to minimize vibration of the apparatus or incorporated into the apparatus in a manner that minimize such vibration. In this respect the mixing means may be housed on one or more vibration dampeners or the apparatus may include one or more vibration dampeners on is base.

Where a mixing means is incorporated into the apparatus the means may be automatically activated upon activation of the heating unit or alternatively there may be a separate activation system. Further, the speed of the mixing may either be fixed or variable. Preferably, there is a separate activation system for the mixing means.

The filter recess incorporated into the apparatus may be of any size or shape that facilitates filtering of a cellular suspension. Further the recess may be adapted to receive and hold at least a tube into which cell suspension may be filtered. Preferably the recess has a conical base providing easy means to access the full volume of cell suspension after it has been filtered.

Desirably, the third recess is designed to receive a 100 μm cell filter. The third recess can accommodate a 100 μm cell filter connected to a conical tube. Preferably, the tube has area/volume graduations marked on the side.

The apparatus may also include a set of tools required for cell harvesting. It will be appreciated by those skilled in the art that any tools necessary for cell harvesting may be included with the device. Preferably, the set of tools are sterile. As an example only, the set of tools may include a glass vessel of separation enzyme; a sterile solution for suspension of the enzyme; a sterile nutrient solution; scalpel; forceps; syringe; medicine dropper, cell filter; wound dressings and/or spray nozzles. In a highly preferred embodiment, the set of tools are stored in a compartment formed in the first member of the apparatus, which is covered by the second member when not in use.

In a highly preferred embodiment, the device is used to harvest a suspension of cells and apply the cells to a recipient site in the following manner.

An aliquot of sterile water is mixed with a portion of lyophilized separation enzyme and placed in the heating recess. The heating means is then activated which heats the contents (i.e. the enzyme solution) of the container to a working temperature of between 30 and 37° C., preferably between 33 and 37° C. and by way of example 37° C. within 2 minutes and maintains the working temperature for at least 45 minutes. Once an operational temperature has been reached, a sample of tissue taken from a donor site is placed in the enzyme solution and incubated at the working temperature. The tissue sample is incubated for between 5 to 45 minutes. Those skilled in the art would appreciate that the time taken to achieve separation of the layers of the tissue sample is dependent on the thickness and size of the tissue sample and the incubation temperature. Once enzymatic separation of the tissue layers is achieved, the tissue sample is removed to the reservoir and the tissue layers are separated using surgical instrument/s.

A carefully measured aliquot of the second solution is then withdrawn from the fluid containment well by aspiration into a syringe and then applied to the layers. The cells between the layers of tissue are scraped off and suspended by mixing with the nutrient solution. The cell suspension is then collected, preferably using a syringe and cannula.

The harvested suspension of cells is then passed through a cell filter located in the filter recess and the filtered suspension of cells is collected into the filter recess. The reservoir may optionally be rinsed with a further volume of the second solution and this resulting suspension of cells also filtered and collected in the filter recess.

The filtered suspension of cells may then optionally be aspirated into a syringe and applied to the recipient site.

EXAMPLES

Further features of the present invention are more fully described in the following non-limiting Examples. It is to be understood, however, that this detailed description is included solely for the purposes of exemplifying the present invention. It should not be understood in any way as a restriction on the broad description of the invention as set out above.

The following examples are put forth so as to provide those of ordinary skill in the art with a complete disclosure and description of how the compositions and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. The present invention is more particularly described in the following examples which are intended as illustrative only since numerous modifications and variations therein will be apparent to those skilled in the art.

Example 1

Preparation of Recipient Site

To optimize the success of the skin graft, the wound was cleaned and assessed to be of the appropriate depth. Further, blood haemostasis was established and the wound checked for evidence of surrounding cellulitis or infection. Techniques for preparing the area included sharp dissection, dermabrasion or laser-resurfacing.

Donor Site Biopsy

The donor site was chosen to appropriately match the recipient site. The donor site was infiltrated with local anaesthetic and adrenaline underneath the skin near the subcutaneous tissue. This allowed the donor site to be firm and aided in the taking a thin split-thickness biopsy. The dimensions of the biopsy were determined by the size of the surface area of the recipient site to be covered. Typically, the biopsy size has an expansion ratio of 1:10-1:80. In this case, a biopsy size of 2 cm×2 cm was taken from the donor site giving an expansion ratio of 1:60.

Cell Resurfacing Using the Rapid Technique

Treatment of the wound was carried out using the ReCell® Rapid Technique cell harvesting apparatus, which is explained in more detail in Example 2 below. The apparatus contained all the instruments, solutions, enzymes and dressings required for wound treatment.

The heating element was activated by depressing the "start button". Solution (sterile water for injection) (10 ml) was transferred from the supplied plastic vessel marked Solution A into a glass vessel containing the separation enzyme (lyophilized trypsin) to give a final concentration of 0.5% trypsin. The enzyme solution was then mixed together, transferred to a vessel already located in the heating element recess and heated to 37° C.

The vessel containing Solution B (nutrient media) was transferred from its supplied vessel into the fluid containment well.

The previously obtained tissue sample was then placed in the enzyme solution and incubated at 37° C. for between 10 to 15 minutes. After this time, the tissue sample was removed from enzyme solution with a pair of forceps, rinsed by dipping into the fluid containment well containing Solution B and placed with the dermal side down and the epidermal side up in the reservoir.

Solution B was then aspirated from the well into a syringe and dripped from the syringe onto both layers of the biopsy.

The skin layers were separated using forceps. This allowed access to the zone of the dermal-epidermal junction of both surfaces. Cells were scraped from the surfaces to develop a plume of cells in the reservoir. The cells were then mixed in Solution B. The plume of cells was then drawn up into the syringe via a 19 gauge cannula.

The supplied filter (100 μm cell filter) was mounted in the filter recess and the plume of cells in Solution B was passed through the filter. A further small amount of Solution B was then used to rinse the reservoir (e.g., a petri dish) and collect any remaining cells, which were also passed through the filter.

The resulting suspension of cells collected in the conical recess was aspirated into a syringe and a nozzle was attached to the syringe for spraying or dripping on to the wound area.

The wound was re-checked to ensure that it was clean and free of debris and that there was no evidence of bacterial contamination. Further, the wound was checked to determine if haemostasis had been achieved. Once the recipient site was ready, the suspension of cells was applied to the wound surface using the nozzle.

The wound was dressed with Surfasoft™ a woven nylon dressing, which was supplied with the apparatus. The healing of the wound was followed up using standard protocols for skin-graft treatment.

Example 2

Figure 1:
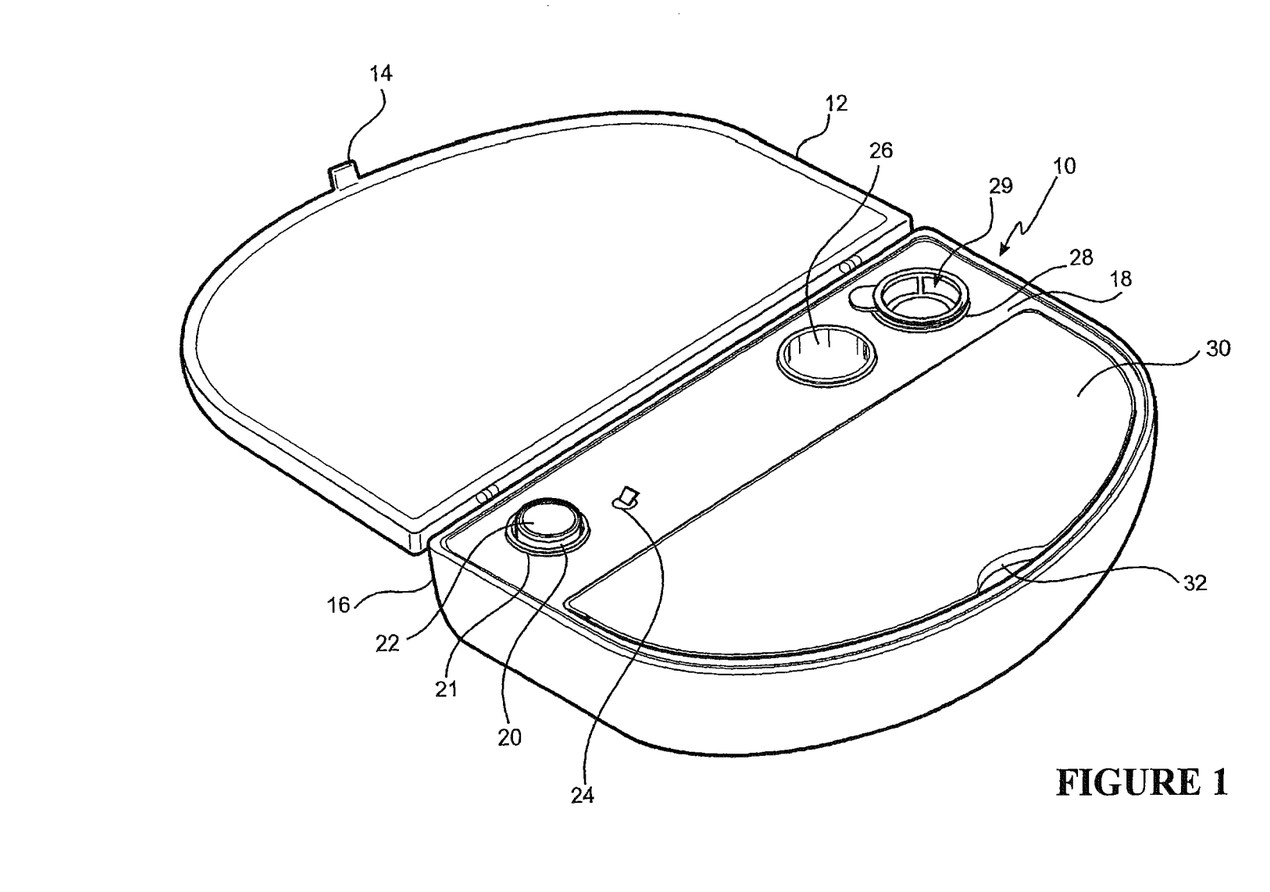
FIG. 1 illustrates a perspective view of the apparatus with the lid open and the second member in place.

The embodiment shown in FIG. 1 is directed to a Re-Cell® Rapid Technique cell harvesting apparatus 10 for use in producing a transplantable cellular suspension of living tissue suitable for grafting to a patient.

As illustrated in FIG. 1 the apparatus includes a closure lid 12 possessing a locking mechanism 14 adapted to releasably engage a base portion 16. The locking mechanism 14 provides a means for closing the apparatus 16 when not in use. Located within the base portion 16 is a first member 18 within which there is provided an aperture 20 in which there is located a vial 22 for the enzyme. Adjacent the aperture there is provided an activation switch 24 capable of activating the heating means (not shown). The first member also provides a fluid containment well 26 and a filter recess 28. As presented in this illustration the filter 29 is shown located in the filter recess. Ordinarily the filter is an optional item included as a separate item in the apparatus.

The aperture 20 in the first member 18 is desirably of such a diameter that it allows the neck of the vial 22 to protrude through and above the first member 18. The periphery of the aperture 20 is fitted with a collar 21 which is slightly smaller than the diameter of the body of the vial 22. Thus, when in use, the vial 22 cannot be removed from the apparatus 10 as it is held in place by the collar 21 located around the periphery of the aperture 20.

Located adjacent to the aperture 20, fluid containment well 26 and filter recess 28 is the second member 30 which is positioned on a seat (not shown) located within a storage compartment (not shown) within the first member 18. When inverted the second member 30 forms a reservoir within which tissue manipulations may be performed. To facilitate separation of the second member 30 from the first member 18 an indent 32 is provided in the side of a portion of the second member 30, which is of such a size that a person can lift the second member from the seat on which it resides in the first member 18.

Within the filter recess 28 there is located a filter 29 (provided separately with the other components) having a mesh therein capable of separating cellular material of greater than 100 μm from a cell supernatant.

Figure 2:
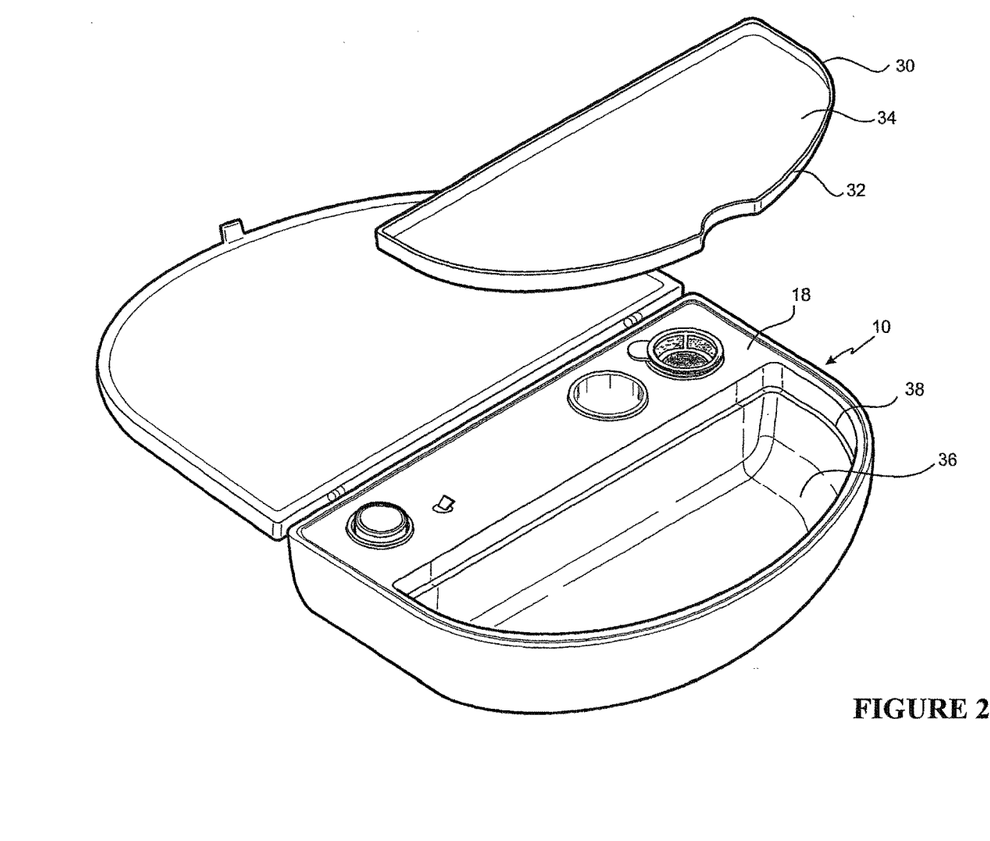
FIG. 2 illustrates a perspective view of the apparatus with the lid open and the second member removed and inverted.

FIG. 2 provides a partially exploded perspective view of the apparatus 10 wherein the second member 30 is removed from the first member 18 and inverted. Inversion of the second member 30 reveals the sidewalls 32 of the second member 30, which form the fluid containment barrier of the reservoir and a reservoir area 34 in which tissue manipulations may be performed.

Removal of the second member 30 from the first member 18 also reveals a storage compartment 36 in the first member 18 in which solutions and tools may be stored when the apparatus 10 is not in use. Within the storage compartment 36 there is located a seat 38 upon which the second member 30 may reside. The seat 38 is preferably located around the periphery of the storage compartment 36 at a depth beneath the surface of the first member 18 that is equivalent to the height of the sidewalls 32 of the second member 30.

Figure 3A:
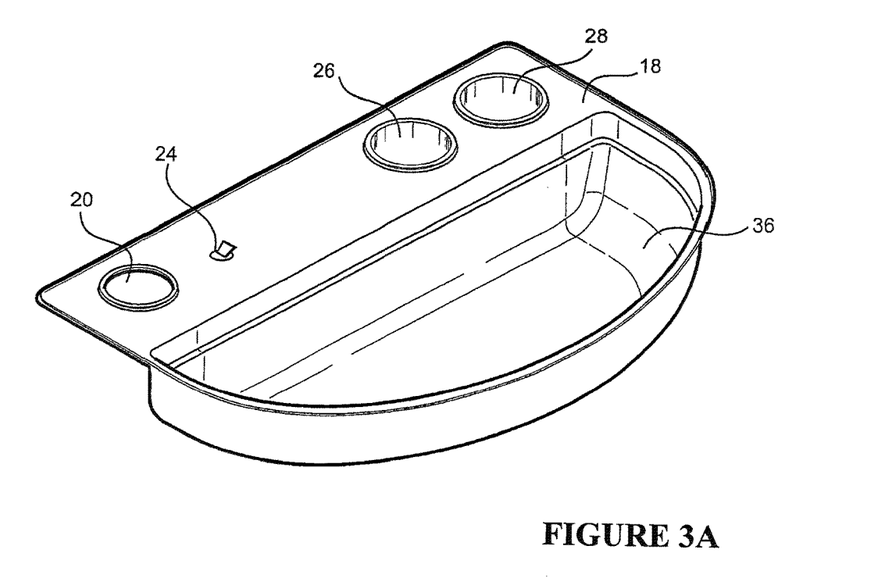
FIG. 3A illustrates a perspective view of the first member of the apparatus.
Figure 3B:
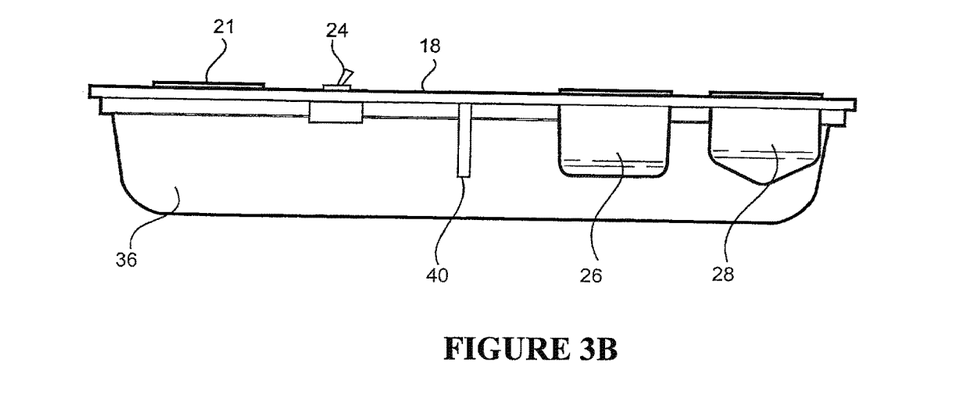
FIG. 3B illustrates a perspective rear view of the first member of the apparatus.

FIG. 3A provides a perspective view of the first member 18 showing the storage compartment 36, the heater activating switch 24, the aperture 20, the fluid containment well 26 and filter recess 28 formed within the first member. FIG. 3B provides a rear view of the first member 18 showing the filter recess 28, the fluid containment well 26, the heater activating switch 24, the aperture collar 21 and the rear wall of the storage compartment 36. As seen in this figure the filter recess has a conical base thereby providing a means for easy access to the cell suspension that is filtered into it. Located adjacent to the fluid containment well and on the opposite side of the filter containment well there is also provided a battery positioning member 40 which protrudes towards the base 16 of the apparatus (not shown) and provides a means for holding the batteries in place, which are required for activating the heating means.

Figure 4:
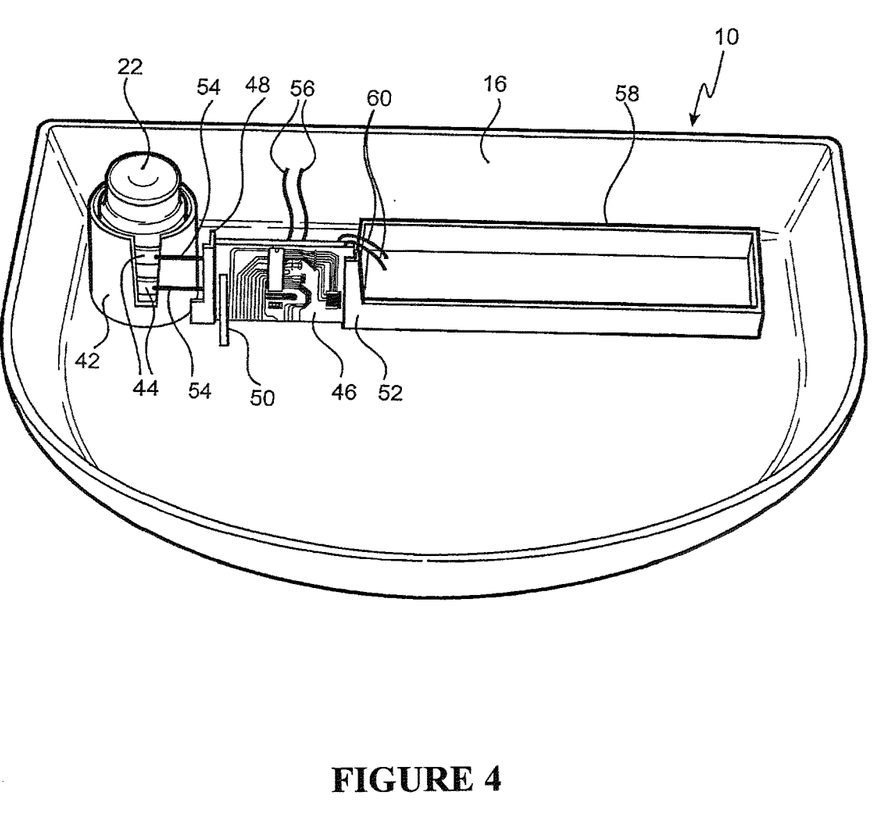
FIG. 4 illustrates a perspective view of the base of the apparatus.

FIG. 4 provides a perspective view of the base 16 of the apparatus 10 showing the vial 22 located within a containment field 42. Between the containment field 42 and the vial 22 there is located a heating collar(s) 44, which surrounds the body of the vial. Adjacent the containment field there is a circuit board 46, which is held in position by circuit board containment means 48, 50 and 52. Said circuit board 46 is in electrical communications with the heating collar(s) 44 by wires 54. The circuit board is also in electrical communication via wires 56 with the heater activating switch (not shown). Adjacent the circuit board 46 there is provided a battery containment means 58, which holds 4 AA batteries in immovable position (not shown). The batteries are in electrical communication with the circuit board 46 by wires

60. When the first member 18 is fitted to the base 16 the batteries are held in place by the battery containment means 58, the battery positioning means 40 and the base of each of the fluid containment well 26 and the filter recess 28. Preferably the conical base of the filter recess 28 also protrudes between the batteries therein providing a further means for securing the batteries in immovable position.

Modifications and variations of the described methods and device of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant field in which this invention resides are intended to be within the scope of the following claims.

The invention claimed is:

1. An apparatus for developing peri-operatively to a patient a cell suspension from a skin tissue sample, and for immediately applying the cell suspension to a graft site of the patient, comprising:
 a first member, a second member, a base portion, an enzyme solution comprising an amount of enzyme sufficient to dissociate cellular stratum in a skin tissue sample, and a nutrient solution suitable for direct application to the graft site, wherein the nutrient solution is free of xenogenic serum and used to suspend cells harvested following release from the skin tissue sample; wherein:
 (i) the first member comprises:
  (a) a storage compartment configured to store a set of tools for cell harvesting and a dispersing device configured to apply the cell suspension to the graft site;
  (b) an aperture extending longitudinally through the first member configured to allow a neck of a vial to protrude through the first member and arranged above a heating unit configured to heat the vial containing the enzyme solution to a predetermined temperature and maintain the predetermined temperature, wherein the enzyme solution, after being heated, is used to incubate the skin tissue sample to dissociate the cellular stratum therein, without encouraging in vitro cellular multiplication; and
  (c) a filter recess comprising a filter means of a filter size between 50 μm and 200 μm, configured to remove cellular congregates greater than the filter size from cells harvested from the skin tissue sample, to form the cell suspension that is suitable for immediate dispersion to the graft site;
 (ii) the first member is located within the base portion, and the base portion comprises:
  (a) the heating unit; and
  (b) a containment field sized to fit the vial to be heated by the heating unit; and
 (iii) the second member is seated within the first member and the second member comprises:
  a top surface, an underside, and sidewalls, such that when inverted, the sidewalls extend upward and comprise a reservoir area configured to withhold the skin tissue sample and at least a portion of the nutrient solution in fluid containment, wherein the reservoir area is of sufficient size to permit manipulation of the skin tissue sample, permitting separation of the cellular stratum and harvesting of cells from the cellular stratum suitable for grafting, without encouraging in vitro cellular multiplication.

2. The apparatus of claim 1, wherein the aperture further houses the vial protruding therethrough and into which the skin tissue sample may be placed for exposure to the enzyme solution.

3. The apparatus of claim 1, wherein the heating unit is controlled by circuitry permitting activation of the heater when required.

4. The apparatus of claim 1, wherein the heating unit is operably linked to a timer mechanism adapted to heat the enzyme solution for a pre-defined period of time.

5. The apparatus of claim 1, wherein the heating unit is provided with an adjustable temperature control.

6. The apparatus of claim 1, further comprising a monitoring means that are capable of indicating that the enzyme solution has reached the predetermined temperature, and/or the amount of time that the enzyme has been in the enzyme solution for.

7. The apparatus of claim 1, further comprising a means to facilitate mixing of the enzyme solution.

8. The apparatus of claim 1, wherein the filter recess is adapted to receive and hold a tube into which the cell suspension may be filtered.

9. The apparatus of claim 1, wherein the fluid containment well serves as a receptacle for a container that holds the nutrient solution.

10. The apparatus of claim 1, wherein the set of tools include a vessel of the enzyme, a sterile solution for suspension of the enzyme, scalpel, forceps, syringe, medicine dropper, cell filter, and/or wound dressings.

11. The apparatus of claim 1, wherein the predetermined temperature is between 30 and 37° C.

12. The apparatus of claim 11, wherein the heating unit maintains the predetermined temperature for at least 45 minutes.

13. The apparatus of claim 1, wherein the heating unit is a heating pad or heating collar.

14. The apparatus of claim 1, wherein the nutrient solution is physiological saline.

15. The apparatus of claim 1, further comprising a closure lid having a locking mechanism adapted to releasably engage the base portion.

16. The apparatus of claim 1, wherein the storage compartment comprises a seat located around its periphery extending from its inner wall at a depth beneath a surface of the first member that is equivalent to a height of the sidewalls of the second member such that the second member may reside in the storage compartment.

17. The apparatus of claim 1, wherein the second member further comprises an indent configured to permit lifting of the second member.

18. The apparatus of claim 1, wherein the dispersing device selected from spray nozzle, pipette, eye-dropper, syringe and/or needle.

19. The apparatus of claim 1, wherein the first member further comprises a fluid containment well configured to store the nutrient solution.

* * * * *